(12) United States Patent
Ruhling et al.

(10) Patent No.: US 10,485,530 B2
(45) Date of Patent: Nov. 26, 2019

(54) ORTHOPEDIC SURGICAL INSTRUMENT FOR KNEE SURGERY

(71) Applicant: DEPUY IRELAND UNLIMITED COMPANY, Ringaskiddy, Co Cork (IE)

(72) Inventors: Marc E. Ruhling, Goshen, IN (US); Jason T. Sherman, Warsaw, IN (US); Duncan G. Young, Yorkshire (GB); Matthew Leyden, St. Paul, MN (US)

(73) Assignee: DePuy Ireland Unlimited Company, Ringaskiddy, Co Cork (IE)

( * ) Notice: Subject to any disclaimer, the term of this patent is extended or adjusted under 35 U.S.C. 154(b) by 747 days.

(21) Appl. No.: 15/202,271

(22) Filed: Jul. 5, 2016

(65) Prior Publication Data

US 2016/0310122 A1    Oct. 27, 2016

Related U.S. Application Data

(62) Division of application No. 13/434,207, filed on Mar. 29, 2012, now Pat. No. 9,381,011.

(51) Int. Cl.
*A61B 17/02* (2006.01)
*A61B 17/88* (2006.01)
(Continued)

(52) U.S. Cl.
CPC ........ *A61B 17/025* (2013.01); *A61B 17/8875* (2013.01); *A61B 17/66* (2013.01);
(Continued)

(58) Field of Classification Search
CPC .... A61B 17/8875; A61B 17/025; A61B 17/66
See application file for complete search history.

(56) References Cited

U.S. PATENT DOCUMENTS

| 4,501,266 A | 2/1985 | McDaniel |
| 4,566,448 A | 1/1986 | Rohr, Jr. |

(Continued)

FOREIGN PATENT DOCUMENTS

| DE | 10335410 A1 | 2/2005 |
| EP | 0645984 | 4/1995 |

(Continued)

OTHER PUBLICATIONS

English translation of Japanese Office Action, Japanese Application No. 2010-077089, dated May 22, 2014, 3 pages.

(Continued)

*Primary Examiner* — Si Ming Ku
(74) *Attorney, Agent, or Firm* — Barnes & Thornburg LLP

(57) ABSTRACT

An orthopedic surgical instrument for use in knee surgeries includes an elongated body, a pair of output shafts, and a user control. A first output shaft extends out from a first side of the body along a first output axis substantially perpendicular to a longitudinal axis of the elongated body. A second output shaft also extends out from the first side of the elongated body along a second output axis substantially perpendicular to the longitudinal axis of the elongated body. The user control is coupled to the elongated body near a first end and the first and second output shafts are situated near the second end of the elongated body. Each of the first output shaft and the second output shaft are configured to turn independent of one another in response to operation of the user control. Various joint distractors for use with the orthopaedic surgical instrument are also disclosed.

20 Claims, 11 Drawing Sheets

(51) Int. Cl.
    *A61B 17/66*        (2006.01)
    *A61B 17/00*        (2006.01)
(52) U.S. Cl.
    CPC .............. *A61B 2017/00685* (2013.01); *A61B 2017/0268* (2013.01)

(56) References Cited

U.S. PATENT DOCUMENTS

| | | |
|---|---|---|
| 4,795,473 A | 1/1989 | Grimes |
| 4,796,610 A | 1/1989 | Cromartie |
| 4,804,000 A | 2/1989 | Lamb et al. |
| 4,808,186 A | 2/1989 | Smith |
| 4,822,362 A | 4/1989 | Walker |
| 4,825,857 A | 5/1989 | Kenna |
| 4,828,562 A | 5/1989 | Kenna |
| 4,834,057 A | 5/1989 | McLeod |
| 4,856,993 A | 8/1989 | Maness et al. |
| 4,888,021 A | 12/1989 | Forte |
| 4,892,093 A | 1/1990 | Zarnowski et al. |
| 4,892,546 A | 1/1990 | Kotz et al. |
| 4,899,761 A | 2/1990 | Brown et al. |
| 4,907,578 A | 3/1990 | Petersen |
| 4,926,847 A | 5/1990 | Luckman |
| 4,932,974 A | 6/1990 | Pappas et al. |
| 4,935,023 A | 6/1990 | Whiteside et al. |
| 4,936,853 A | 6/1990 | Fabian et al. |
| 4,938,762 A | 7/1990 | Wehrli |
| 4,944,756 A | 7/1990 | Kenna |
| 4,959,071 A | 9/1990 | Brown et al. |
| 4,963,153 A | 10/1990 | Noesberger et al. |
| 4,973,331 A | 11/1990 | Pursley et al. |
| 4,979,949 A | 12/1990 | Matsen et al. |
| 4,986,281 A | 1/1991 | Preves et al. |
| 5,002,547 A | 3/1991 | Poggie et al. |
| 5,018,514 A | 5/1991 | Grood et al. |
| 5,020,797 A | 6/1991 | Burns |
| 5,032,132 A | 7/1991 | Matsen |
| 5,033,291 A | 7/1991 | Podoloff et al. |
| 5,037,423 A | 8/1991 | Kenna |
| 5,056,530 A | 10/1991 | Butler et al. |
| 5,080,675 A | 1/1992 | Lawes et al. |
| 5,082,003 A | 1/1992 | Lamb et al. |
| 5,098,436 A | 3/1992 | Ferrante et al. |
| 5,122,144 A | 6/1992 | Bert et al. |
| 5,125,408 A | 6/1992 | Basser |
| 5,129,909 A | 7/1992 | Sutherland |
| 5,133,660 A | 7/1992 | Fenick |
| 5,197,488 A | 3/1993 | Kovacevic |
| 5,207,711 A | 5/1993 | Caspari et al. |
| 5,213,112 A | 5/1993 | Niwa |
| 5,228,459 A | 7/1993 | Caspari et al. |
| 5,234,433 A | 8/1993 | Bert |
| 5,234,434 A | 8/1993 | Goble |
| 5,234,435 A | 8/1993 | Seagrave |
| 5,236,432 A | 8/1993 | Matsen et al. |
| 5,250,050 A | 10/1993 | Poggie et al. |
| 5,257,996 A | 11/1993 | McGuire |
| 5,312,411 A | 5/1994 | Steele et al. |
| 5,320,529 A | 6/1994 | Pompa |
| 5,326,363 A | 7/1994 | Aikins |
| 5,329,933 A | 7/1994 | Graf |
| 5,342,367 A | 8/1994 | Ferrante et al. |
| 5,358,527 A | 10/1994 | Forte |
| 5,360,016 A | 11/1994 | Kovacevic |
| 5,364,401 A | 11/1994 | Ferrante |
| 5,364,402 A | 11/1994 | Mumme |
| 5,395,401 A | 3/1995 | Bahler |
| 5,402,793 A | 4/1995 | Gruner |
| 5,403,319 A | 4/1995 | Matsen et al. |
| 5,417,694 A | 5/1995 | Marik et al. |
| 5,423,334 A | 6/1995 | Jordan |
| 5,425,775 A | 6/1995 | Kovacevic |
| 5,431,652 A | 7/1995 | Shimamoto et al. |
| 5,431,653 A | 7/1995 | Callaway |
| 5,443,518 A | 8/1995 | Insall |
| 5,456,724 A | 10/1995 | Yen et al. |
| 5,470,354 A | 11/1995 | Hershberger et al. |
| 5,489,311 A | 2/1996 | Cipolletti |
| 5,496,352 A | 3/1996 | Renger |
| 5,514,144 A | 5/1996 | Bolton |
| 5,514,183 A | 5/1996 | Epstein |
| 5,520,695 A | 5/1996 | Luckman |
| 5,540,696 A | 7/1996 | Booth et al. |
| 5,562,674 A | 10/1996 | Stalcup et al. |
| 5,569,261 A | 10/1996 | Marik et al. |
| 5,571,110 A | 11/1996 | Matsen et al. |
| 5,571,197 A | 11/1996 | Insall |
| 5,597,379 A | 1/1997 | Haines |
| 5,611,774 A | 3/1997 | Postelmans |
| 5,613,971 A | 3/1997 | Lower |
| 5,630,820 A | 5/1997 | Todd |
| 5,643,272 A | 7/1997 | Haines |
| 5,649,929 A | 7/1997 | Callaway |
| 5,656,785 A | 8/1997 | Trainor et al. |
| 5,658,293 A | 8/1997 | Vanlaningham |
| 5,669,914 A | 9/1997 | Eckhoff |
| 5,671,695 A | 9/1997 | Schroeder |
| 5,682,886 A | 11/1997 | Delp et al. |
| 5,683,397 A | 11/1997 | Vendrely et al. |
| 5,688,280 A | 11/1997 | Booth, Jr. et al. |
| 5,688,282 A | 11/1997 | Baron et al. |
| 5,690,635 A | 11/1997 | Matsen et al. |
| 5,702,422 A | 12/1997 | Stone |
| 5,702,463 A | 12/1997 | Pothier et al. |
| 5,733,292 A | 3/1998 | Gustilo et al. |
| 5,735,904 A | 4/1998 | Pappas |
| 5,743,909 A | 4/1998 | Collette |
| 5,768,134 A | 6/1998 | Swaelens et al. |
| 5,769,894 A | 6/1998 | Ferragamo |
| 5,782,925 A | 7/1998 | Collazo et al. |
| 5,800,438 A | 9/1998 | Tuke |
| 5,800,552 A | 9/1998 | Forte |
| 5,810,827 A | 9/1998 | Haines |
| 5,824,085 A | 10/1998 | Sahay et al. |
| 5,824,104 A | 10/1998 | Tuke |
| 5,833,616 A | 11/1998 | Gruner et al. |
| 5,840,047 A | 11/1998 | Stedham |
| 5,860,980 A | 1/1999 | Axelson et al. |
| 5,871,018 A | 2/1999 | Delp et al. |
| 5,879,389 A | 3/1999 | Koshino |
| 5,880,976 A | 3/1999 | DiGioia, III et al. |
| 5,891,150 A | 4/1999 | Chan |
| 5,911,723 A | 6/1999 | Ashby |
| 5,931,777 A | 8/1999 | Sava |
| 5,935,086 A | 8/1999 | Beacon et al. |
| 5,976,147 A | 11/1999 | LaSalle et al. |
| 6,013,103 A | 1/2000 | Kaufman et al. |
| 6,019,767 A | 2/2000 | Howell |
| 6,022,377 A | 2/2000 | Nuelle et al. |
| 6,034,296 A | 3/2000 | Elvin et al. |
| 6,056,752 A | 5/2000 | Roger |
| 6,056,754 A | 5/2000 | Haines et al. |
| 6,056,756 A | 5/2000 | Eng et al. |
| 6,080,154 A | 6/2000 | Reay-Young et al. |
| 6,086,592 A | 7/2000 | Rosenberg et al. |
| 6,096,043 A | 8/2000 | Techiera et al. |
| 6,102,952 A | 8/2000 | Koshino |
| 6,113,604 A | 9/2000 | Whittaker et al. |
| 6,126,692 A | 10/2000 | Robie et al. |
| 6,165,142 A | 12/2000 | Bar |
| 6,174,294 B1 | 1/2001 | Crabb et al. |
| 6,236,876 B1* | 5/2001 | Gruner ................ A61B 1/0052 600/114 |
| 6,327,491 B1 | 12/2001 | Franklin et al. |
| 6,447,448 B1 | 9/2002 | Ishikawa et al. |
| 6,488,711 B1 | 12/2002 | Grafinger |
| 6,540,787 B2 | 4/2003 | Biegun et al. |
| 6,553,681 B2 | 4/2003 | Ekholm, Jr. et al. |
| 6,575,980 B1 | 6/2003 | Robie et al. |
| 6,589,283 B1 | 7/2003 | Metzger et al. |
| 6,610,096 B2 | 8/2003 | MacDonald |
| 6,632,225 B2 | 10/2003 | Sanford et al. |
| 6,645,215 B1 | 11/2003 | McGovern et al. |
| 6,648,896 B2 | 11/2003 | Overes et al. |

(56) References Cited

U.S. PATENT DOCUMENTS

| | | |
|---|---|---|
| 6,702,821 B2 | 3/2004 | Bonutti |
| 6,706,005 B2 | 3/2004 | Roy et al. |
| 6,758,850 B2 | 7/2004 | Smith et al. |
| 6,770,078 B2 | 8/2004 | Bonutti |
| 6,821,299 B2 | 11/2004 | Kirking et al. |
| 6,827,723 B2 | 12/2004 | Carson |
| 6,856,834 B2 | 2/2005 | Treppo et al. |
| 6,905,513 B1 | 6/2005 | Metzger |
| 6,923,817 B2 | 8/2005 | Carson et al. |
| 6,972,039 B2 | 12/2005 | Metzger et al. |
| 6,974,481 B1 | 12/2005 | Carson |
| 6,984,249 B2 | 1/2006 | Keller |
| 7,104,996 B2 | 9/2006 | Bonutti |
| 7,153,281 B2 | 12/2006 | Holmes |
| 7,232,416 B2 | 6/2007 | Czernicki |
| 7,275,218 B2 | 9/2007 | Petrella et al. |
| 7,333,013 B2 | 2/2008 | Berger |
| 7,362,228 B2 | 4/2008 | Nycz et al. |
| 7,412,897 B2 | 8/2008 | Crottet et al. |
| 7,544,211 B2 | 6/2009 | Rochetin |
| 7,559,931 B2 | 7/2009 | Stone |
| 7,575,602 B2 | 8/2009 | Amirouche et al. |
| 7,615,005 B2 | 11/2009 | Stefanchik et al. |
| 7,615,055 B2 | 11/2009 | Stefanchik et al. |
| 7,632,283 B2 | 12/2009 | Heldreth |
| 7,794,499 B2 | 9/2010 | Navarro et al. |
| 7,849,751 B2 | 12/2010 | Clark et al. |
| 7,854,766 B2 | 12/2010 | Moskowitz et al. |
| 7,892,236 B1 | 2/2011 | Bonutti |
| 7,932,825 B2 | 4/2011 | Berger |
| 8,082,162 B2 | 12/2011 | Flood |
| 8,112,175 B2 | 2/2012 | Handfield et al. |
| 8,118,815 B2 | 2/2012 | van der Walt |
| 8,133,232 B2 | 3/2012 | Levy et al. |
| 8,211,041 B2 | 7/2012 | Fisher et al. |
| 8,231,631 B2 | 7/2012 | Lavallee et al. |
| 8,444,697 B1 | 5/2013 | Butler |
| 9,381,011 B2 | 7/2016 | Ruhling |
| 2001/0021877 A1 | 9/2001 | Biegun et al. |
| 2002/0007294 A1 | 1/2002 | Bradbury et al. |
| 2002/0029045 A1 | 3/2002 | Bonutti |
| 2002/0052606 A1 | 5/2002 | Bonutti |
| 2002/0133175 A1 | 9/2002 | Carson |
| 2002/0147455 A1 | 10/2002 | Carson |
| 2002/0156480 A1 | 10/2002 | Overes et al. |
| 2003/0028196 A1 | 2/2003 | Bonutti |
| 2003/0069591 A1 | 4/2003 | Carson et al. |
| 2003/0069644 A1 | 4/2003 | Kovacevic |
| 2003/0130665 A1 | 7/2003 | Pinczewski |
| 2003/0139645 A1 | 7/2003 | Adelman |
| 2003/0144669 A1 | 7/2003 | Robinson |
| 2003/0153978 A1 | 8/2003 | Whiteside |
| 2003/0187452 A1 | 10/2003 | Smith et al. |
| 2003/0236472 A1 | 12/2003 | Van Hoeck et al. |
| 2004/0019382 A1 | 1/2004 | Amirouche et al. |
| 2004/0064073 A1 | 4/2004 | Heldreth |
| 2004/0064191 A1 | 4/2004 | Wasielewski |
| 2004/0097951 A1 | 5/2004 | Steffensmeier |
| 2004/0122441 A1 | 6/2004 | Muratsu |
| 2004/0153091 A1 | 8/2004 | Figueroa et al. |
| 2004/0243148 A1 | 12/2004 | Wasielewski |
| 2005/0010213 A1 | 1/2005 | Stad |
| 2005/0010302 A1 | 1/2005 | Dietz et al. |
| 2005/0021044 A1 | 1/2005 | Stone et al. |
| 2005/0038442 A1 | 2/2005 | Freeman |
| 2005/0085920 A1 | 4/2005 | Williamson |
| 2005/0113846 A1 | 5/2005 | Carson |
| 2005/0149041 A1 | 7/2005 | McGinley et al. |
| 2005/0177169 A1 | 8/2005 | Fisher et al. |
| 2005/0177170 A1 | 8/2005 | Fisher et al. |
| 2005/0177173 A1 | 8/2005 | Aebi et al. |
| 2005/0234332 A1 | 10/2005 | Murphy |
| 2005/0234448 A1 | 10/2005 | McCarthy |
| 2005/0234465 A1 | 10/2005 | McCombs |
| 2005/0234466 A1 | 10/2005 | Stallings |
| 2005/0234468 A1 | 10/2005 | Carson |
| 2005/0251026 A1 | 11/2005 | Stone |
| 2005/0261071 A1 | 11/2005 | Cameron |
| 2005/0267485 A1 | 12/2005 | Cordes et al. |
| 2005/0267486 A1 | 12/2005 | Cordes et al. |
| 2006/0012736 A1 | 1/2006 | Nishino et al. |
| 2006/0081063 A1 | 4/2006 | Neubauer et al. |
| 2006/0149277 A1 | 7/2006 | Cinquin et al. |
| 2006/0155295 A1 | 7/2006 | Supper |
| 2006/0161051 A1 | 7/2006 | Terrill-Grisoni et al. |
| 2006/0219776 A1 | 10/2006 | Finn |
| 2006/0224088 A1 | 10/2006 | Roche |
| 2006/0232408 A1 | 10/2006 | Nycz |
| 2006/0241569 A1 | 10/2006 | DiSilvestro |
| 2006/0271056 A1 | 11/2006 | Terrill-Grisoni et al. |
| 2007/0073405 A1 | 3/2007 | Verhulst |
| 2007/0162142 A1 | 7/2007 | Stone |
| 2007/0219561 A1 | 9/2007 | Lavallee et al. |
| 2007/0225704 A1 | 9/2007 | Ziran et al. |
| 2007/0233144 A1 | 10/2007 | Lavallee |
| 2007/0239165 A1 | 10/2007 | Amirouche |
| 2007/0244488 A1 | 10/2007 | Metzger et al. |
| 2007/0293868 A1 | 12/2007 | Delfosse et al. |
| 2008/0051892 A1 | 2/2008 | Malandain |
| 2008/0091272 A1 | 4/2008 | Aram et al. |
| 2008/0114463 A1 | 5/2008 | Auger et al. |
| 2008/0133022 A1 | 6/2008 | Caylor |
| 2008/0188934 A1 | 8/2008 | Moser |
| 2008/0242937 A1 | 10/2008 | DiNucci |
| 2008/0306413 A1 | 12/2008 | Crottet et al. |
| 2009/0005708 A1 | 1/2009 | Johanson |
| 2009/0018544 A1 | 1/2009 | Heavener |
| 2009/0088674 A1 | 4/2009 | Caillouette et al. |
| 2009/0088760 A1 | 4/2009 | Aram et al. |
| 2009/0099570 A1 | 4/2009 | Paradis et al. |
| 2009/0138019 A1 | 5/2009 | Wasielewski |
| 2009/0138021 A1 | 5/2009 | Colquhoun |
| 2009/0222089 A1 | 9/2009 | Hauri et al. |
| 2009/0266728 A1 | 10/2009 | Turner et al. |
| 2009/0270869 A1 | 10/2009 | Colquhoun et al. |
| 2009/0318836 A1 | 12/2009 | Stone et al. |
| 2009/0318930 A1 | 12/2009 | Stone et al. |
| 2009/0318931 A1 | 12/2009 | Stone et al. |
| 2009/0326544 A1 | 12/2009 | Chessar et al. |
| 2010/0016705 A1 | 1/2010 | Stone |
| 2010/0063508 A1 | 3/2010 | Borja et al. |
| 2010/0063509 A1 | 3/2010 | Borja et al. |
| 2010/0064216 A1 | 3/2010 | Borja et al. |
| 2010/0069911 A1 | 3/2010 | Borja et al. |
| 2010/0076505 A1 | 3/2010 | Borja |
| 2010/0137869 A1 | 6/2010 | Borja et al. |
| 2010/0137871 A1 | 6/2010 | Borja |
| 2010/0179558 A1 | 7/2010 | Quirno |
| 2010/0194541 A1 | 8/2010 | Stevenson et al. |
| 2010/0198275 A1 | 8/2010 | Chana et al. |
| 2010/0217156 A1 | 8/2010 | Fisher et al. |
| 2010/0249533 A1 | 9/2010 | Pierce et al. |
| 2010/0249658 A1 | 9/2010 | Sherman et al. |
| 2010/0249659 A1 | 9/2010 | Sherman et al. |
| 2010/0249660 A1 | 9/2010 | Sherman et al. |
| 2010/0249777 A1 | 9/2010 | Sherman et al. |
| 2010/0249789 A1 | 9/2010 | Rock et al. |
| 2010/0250571 A1 | 9/2010 | Pierce et al. |
| 2011/0251694 A1 | 10/2011 | Wasielewski |
| 2013/0138112 A1 | 5/2013 | Young |
| 2013/0261502 A1 | 10/2013 | Sherman et al. |
| 2013/0261503 A1 | 10/2013 | Sherman et al. |
| 2013/0261505 A1 | 10/2013 | Sherman et al. |
| 2014/0018707 A1 | 1/2014 | Sherman et al. |

FOREIGN PATENT DOCUMENTS

| | | |
|---|---|---|
| EP | 0756735 | 2/1997 |
| EP | 0720834 B1 | 6/1999 |
| EP | 0979636 A2 | 2/2000 |
| EP | 1129676 | 9/2001 |
| EP | 1245193 | 10/2002 |
| EP | 1348382 A2 | 10/2003 |
| EP | 1402857 A2 | 3/2004 |

(56) References Cited

FOREIGN PATENT DOCUMENTS

| | | |
|---|---|---|
| EP | 1645229 | 4/2006 |
| EP | 1707159 A1 | 10/2006 |
| EP | 1800616 A1 | 6/2007 |
| EP | 1915951 A2 | 4/2008 |
| FR | 2897528 A1 | 8/2007 |
| JP | 53-135699 U | 10/1978 |
| JP | 56173483 U | 12/1981 |
| JP | 02-111660 | 4/1990 |
| JP | 03103163 U | 10/1991 |
| JP | 2000-513263 A | 10/2000 |
| JP | 2006-158722 A | 6/2006 |
| JP | 2007-54488 A | 3/2007 |
| JP | 2008-126085 A | 6/2008 |
| WO | 7900739 | 10/1979 |
| WO | WO 93/25157 A1 | 12/1993 |
| WO | WO 95/28688 A1 | 10/1995 |
| WO | 96/17552 A1 | 6/1996 |
| WO | 199808429 | 3/1998 |
| WO | 9935972 A1 | 7/1999 |
| WO | 0078225 A1 | 12/2000 |
| WO | 02071924 A2 | 9/2002 |
| WO | 03065949 A2 | 8/2003 |
| WO | 03084412 A1 | 10/2003 |
| WO | 2004008988 A2 | 1/2004 |
| WO | 2005023120 A1 | 3/2005 |
| WO | 2005089681 A2 | 9/2005 |
| WO | 2007/036694 A1 | 4/2007 |
| WO | 2007/036699 A1 | 4/2007 |
| WO | 2009045960 A1 | 4/2009 |
| WO | 2009105479 | 8/2009 |
| WO | 2010/011978 A1 | 1/2010 |
| WO | 2010/022272 A1 | 2/2010 |
| WO | 2010/030809 A1 | 3/2010 |
| WO | 2011011609 A2 | 1/2011 |
| WO | 2011128657 A1 | 10/2011 |
| WO | 2012004580 A1 | 1/2012 |

OTHER PUBLICATIONS

European Search Report for European Patent Application 10156105.8-2319, dated Jun. 15, 2010, 8 pgs.
European Search Report for European Patent Application 06251808.9-2310, dated Jul. 14, 2006, 7 pgs.
European Search Report for European Application No. 13161258.2-1654, dated May 15, 2013, 7 pages.
A-tech Instruments Ltd. http://web.archive.org/web/20090210153037/http://a-tech.ca/subcat.php?id=8 (Jul. 9, 2014).
A-tech Instruments Ltd. http://web.archive.org/web/20090210153037/http://a-tech.ca/subcat.php?id=8 (Feb. 10, 2009).
European Search Report, European Application No. 15150434.7-1654, dated Apr. 24, 2015, 6 pages.
Pierce et al., "Sensored Dynamic Distractor Instrument", U.S. Appl. No. 61/211,023, filed Mar. 26, 2009, 10 pages.
"Custom Fit Total Knee Replacement Surgery", http://web.archive.org/web/20080820181712/http://www.customfittotalknee.com/conventional_knee_replacement.htm, Aug. 2008.
European Search Report for European Patent Application No. 13161810.0-1654, dated Jul. 8, 2013, 7 pages.
Rademacher et al., Computer Assisted Orothopaedic Surgery with Image Based Individual Templates, Clinical Orthopaedics and Related Research, 354, 28-38, 1998.
Hafez et al., "Computer-assisted Total Knee Arthoplasty Using Patient-specific Templating", Clinical Orthopaedics and Related Research, 444, 184-192, 2006.
European Search Report, European Patent Application No. 10156120.7-2201, dated Jul. 7, 2010, 6 pages.
European Communication pursuant to Article 94(3) EPC, European Patent Application No. 10156105.8-2319, dated Aug. 1, 2012, 5 pages.
European Search Report, European Patent Application No. 10156132.2-2201, dated Jul. 12, 2010, 6 pages.
European Search Report, European Patent Application No. 10156128.0-1526/2237014, dated Dec. 13, 2012, 6 pages.
Jian Wu et al., A Method for Widening the Range of Force Measurement and Gap Adjustment in the Total Knee Replacement, International Conference on BioMedical Engineering and Informatics, 2008, 4 pages.
European Search Report, European Patent Application No. 10156128.0-1506, dated Mar. 1, 2013, 11 pages.
European Search Report, European Patent Application No. 13161812.6-1654, dated Jun. 11, 2013, 7 pages.
European Communication pursuant to Article 94(3) EPC, European Application No. 10156120.7-2201, dated Jan. 17, 2013, 4 pages.
European Search Report, European Patent Application No. 10156120.7-2201, dated Jan. 17, 2013, 4 pages.
European Search Report, European Patent Application No. 10156132.2-2201, dated Jan. 16, 2013, 4 pages.
Search Report and Written Opinion from the State Intellectual Property Office of the People's Republic of China for Application No. 201010158674.6, dated May 30, 2014, 12 pages.
English translation of Japanese Office Action, Japanese Application No. 2013-068396, dated Feb. 14, 2017, 8 pages.

* cited by examiner

ORTHOPEDIC SURGICAL INSTRUMENT FOR KNEE SURGERY

This divisional application claims priority under 35 U.S.C. § 121 to U.S. patent application Ser. No. 13/434,207, now U.S. Pat. No. 9,381,011, which was filed on Mar. 29, 2012 and is expressly incorporated herein by reference.

TECHNICAL FIELD

The present disclosure relates generally to surgical instruments, and more particularly, to surgical instruments for use during knee surgeries such as total knee arthroscopy.

BACKGROUND

In some orthopedic surgical procedures, such as total knee arthroscopy, surgical instruments generally known as knee distractors have been developed for orienting a patient's knee joint. For example, in a total knee replacement procedure, controlling the relative positions of a patient's tibia and femur during surgery allows a surgeon to set the orientation of the knee joint and obtain predetermined anatomic and mechanical axes along which the knee joint will operate after surgery.

In order to control the relative position of a patient's tibia and femur, a knee distractor may be inserted between the proximal end of the tibia and the distal end of the femur and operated to space the tibia from the femur to set the orientation and joint space of the knee joint. Some knee distractors can be operated to independently space lateral and medial sides of the tibia and femur to obtain a predetermined orientation of the knee joint.

Some distractors may include sensors or scales to measure the joint force of the patient's knee joint during the distraction process. Such distractors are commonly known as ligament balancers. During operation, a ligament balancer may be used to help balance the surrounding soft tissue (i.e., ligaments) of a patient's joint. For example, in a total knee replacement procedure, ligament balancing may be performed to ensure a generally rectangular shaped extension gap and a generally rectangular shaped flexion gap at a predetermined joint force value between the patient's natural or prosthetic proximal tibia and the patient's natural or prosthetic distal femur.

To do so, a ligament balancer may be positioned between a patient's tibia and femur, similar to a standard distractor, to measure the medial and lateral joint forces and the medial and/or lateral gap displacements when the patient's leg is in extension (i.e., the patient's tibia is positioned at about 0 degrees relative to the patient's femur) and in flexion (i.e., the patient's tibia is positioned at about 90 degrees relative to the patient's femur). In either extension or flexion, if the medial and lateral gap displacements are not approximately equal (i.e., do not form a generally rectangular shaped joint gap) at the predetermined joint force value, ligament release may be performed to equalize the medial and/or lateral gap displacements. Sometimes use of a knee distractor and a ligament balancer may be difficult for a surgeon or assistant and may require multiple insertion and removal procedures for each to be used during a single surgery.

SUMMARY

According to one aspect of the present disclosure, an orthopedic surgical instrument may include an elongated body, a first output shaft, a second output shaft, and a user control. The elongated body may have a first end and a second end and may include a handle at the first end. The elongated body may also define a longitudinal axis. The first output shaft may extend out from a first side of the elongated body along a first output axis that is substantially perpendicular to the longitudinal axis of the elongated body. The second output shaft may extend out from the first side of the elongated body along a second output axis that is substantially perpendicular to the longitudinal axis of the elongated body. The user control may be coupled to the elongated body near the first end of the elongated body. The first output shaft and the second output shaft may be situated near the second end of the elongated body and may be configured to turn independent of one another in response to operation of the user control.

In some embodiments, the user control may also include a first input and a second input. The first output shaft may be configured to turn in response to a user operating the first input and the second output shaft may be configured to turn in response to a user operating the second input. The first input may include a first pulley housed inside the elongated body and rotatable about a first input axis that extends perpendicular to the longitudinal axis of the elongated body. The second input may include a second pulley housed inside the elongated body and rotatable about a second input axis. The second input axis may be spaced apart from the first input axis that extends perpendicular to the longitudinal axis of the elongated body.

In some embodiments, the orthopedic surgical instrument may also include a first belt linkage connecting the first pulley to the first output shaft and a second belt linkage connecting the second pulley to the second output shaft. It is contemplated that, the first pulley may be movable along the longitudinal axis of the elongated body to tension the first belt linkage and the second pulley may be movable along the longitudinal axis of the elongated body to tension the second belt linkage. The first input may include a knob coupled to the pulley and rotatable about the first input axis.

In some embodiments, the first input may include a knob, an indicator ring, and a gear set. The gear set may be coupled between the knob and the indicator ring so that the indicator ring turns less than one revolution in response to the knob being turned one revolution. It is contemplated that, the first output axis and the second output axis may be coplanar.

In some embodiments, the first output shaft may includes a proximal end coupled to the elongated body and a distal end having a driver head with at least one flat surface extending along the first output axis. The second output shaft may include a proximal end coupled to the elongated body and a distal end having a driver head with at least one flat surface extending along the first output axis.

In some embodiments, the elongated body may be formed to include an access aperture extending through the elongated body. The access aperture may be substantially perpendicular to the longitudinal axis of the elongated body and may be situated between the user control and the second end of the elongated body.

According to another aspect of the present disclosure, an orthopedic surgical instrument may include a joint distractor and a driver. The joint distractor may include a tibial platform, a medial paddle, and a lateral paddle. Each paddle may be configured to be raised and lowered relative to the tibial platform independent of the other paddle. The driver may include an elongated body, a user control coupled to the elongated body, a medial output shaft extending out from the elongated body and operatively coupleable the medial paddle, and a lateral output shaft extending out from the elongated body and operatively coupleable to the lateral paddle. The medial output shaft may be configured to move the medial paddle between a raised position and a lowered position relative to the tibial platform in response to operation of the user control. The lateral output shaft may be configured to move the lateral paddle between a raised position and a lowered position relative to the tibial platform in response to operation of the user control.

In some embodiments, the tibial platform of the joint distractor may include a tibial plate, a medial input, and a lateral input. The medial input may be configured to engage the medial output shaft when the driver is coupled to the joint distractor. The lateral input may be configured to engage the lateral output shaft when the driver is coupled to the joint distractor.

In some embodiments, the joint distractor may include a medial interface block configured to move between an anterior position when the medial paddle is in the lowered position and a posterior position when the medial paddle is in the raised position. The medial interface block may be formed to include a threaded hole extending through the interface block. It is contemplated that the medial paddle may include a ramp surface engaging the medial interface block. The ramp surface of the medial paddle may be a downwardly-facing ramp surface.

In some embodiments, the joint distractor may include a lateral interface block configured to move between an anterior position when the lateral paddle is in the lowered position and a posterior position when the lateral paddle is in the raised position. The lateral paddle may include a ramp surface engaging the lateral interface block.

In some embodiments, the medial paddle may move between an anterior position when the medial paddle is in the lowered potion and a posterior position when the medial paddle is in a raised position. The lateral paddle may move between an anterior position when the lateral paddle is in the lowered potion and a posterior position when the lateral paddle is in a raised position.

In some embodiments, the joint distractor may include a medial swing arm pivotably coupled to the medial paddle and the tibial plate. The joint distractor may also include a lateral swing arm pivotably coupled to the lateral paddle and the tibial plate.

According to another aspect of the present disclosure, an orthopedic surgical instrument may include a joint distractor and a driver. The joint distractor may include a tibial platform, a medial paddle, and a lateral paddle. The driver may be operatively coupleable to the joint distractor and may include a user control situated at a first end and an output shaft situated at a second end. The tibial platform may include a medial input configured to be engaged by the output shaft of the driver and a lateral input configured to be engaged by the output shaft of the driver. Each paddle may be configured to move along an arcuate path between a raised position and a lowered position independent of the other paddle in response to a user coupling the output shaft to one of the inputs and operating the user control.

In some embodiments, the joint distractor may include a medial swing arm pivotably coupled to the medial paddle and the tibial plate. The joint distractor may also include a lateral swing arm pivotably coupled to the lateral paddle and the tibial plate.

The tibial platform may include a tibial plate. Each input may include an input screw situated between the tibial plate and one of the medial and lateral paddles.

DESCRIPTION OF THE DRAWINGS

The systems and methods described herein are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, reference labels have been repeated among the figures to indicate corresponding or analogous elements.

DETAILED DESCRIPTION

Figure 1:
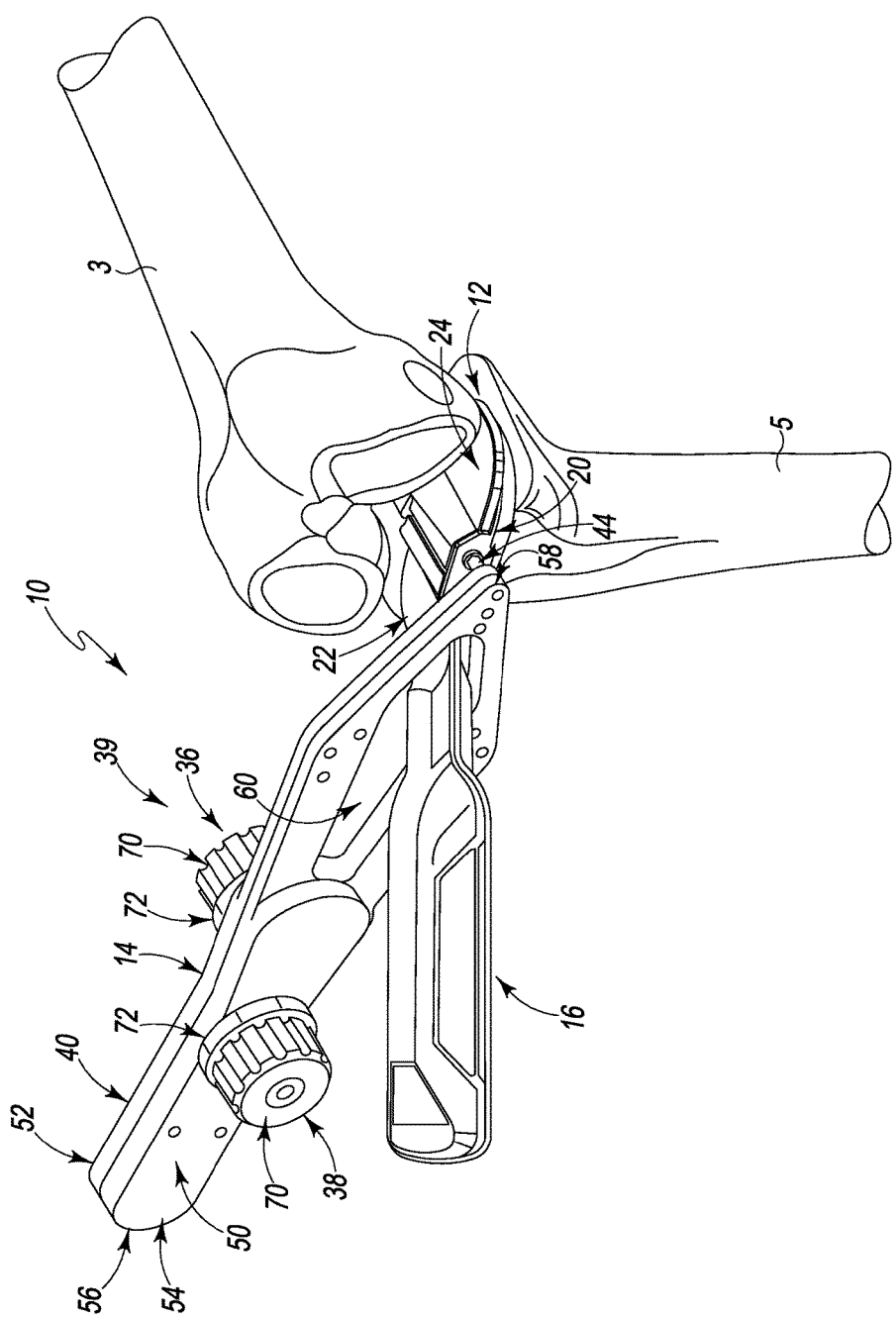
FIG. 1 is a perspective view of a surgical instrumentation system including a joint distractor situated between a patient's tibia and femur, a driver for adjusting the joint distractor, and a sensor for measuring tension in a patient's knee ligaments during adjustment of the joint distractor.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Referring to FIG. 1, a surgical instrumentation system 10 for use during an orthopedic surgery, in particular a knee surgery, is shown positioned relative to a patient's knee joint. The surgical instrumentation system 10 includes a joint distractor 12, a driver 14, and a force sensor module 16. The joint distractor 12 is configured to independently space the lateral and medial condyles of the patient's femur 3 from the proximal end of the patient's tibia 5. As shown in FIG. 1, the driver 14 provides a user interface to an orthopaedic surgeon or other healthcare provider to allow the user to operate the joint distractor 12 while the ligaments and patella extending over the anterior face of the patient's knee joint remain substantially in place. The sensor module 16 includes a plurality of force sensors (not shown) and is configured to measure medial and lateral joint forces between the patient's femur 3 and tibia 5. The sensor module 16 may be used in with the joint distractor 12 and driver 14 to measure joint forces of the patient's knee joint during distraction thereof. In the illustrative embodiment, the sensor module 16 is of the type described in U.S. patent application Ser. Nos. 12/415,172; 12/415,350; 12/415,365; and 12/415,290, each of which was filed on Mar. 31, 2009 and is hereby incorporated by reference herein. However, in other embodiments, other types of sensor modules or other devices may be used in conjunction with the distractor 12 and driver 14 to measure joint forces of the patient's knee joint. It should be appreciated that the concurrent use of the joint distractor 12, driver 14, and sensor module 16 allows a surgeon to simultaneously adjust the orientation of the knee joint and monitor ligament balance.

Figure 2:
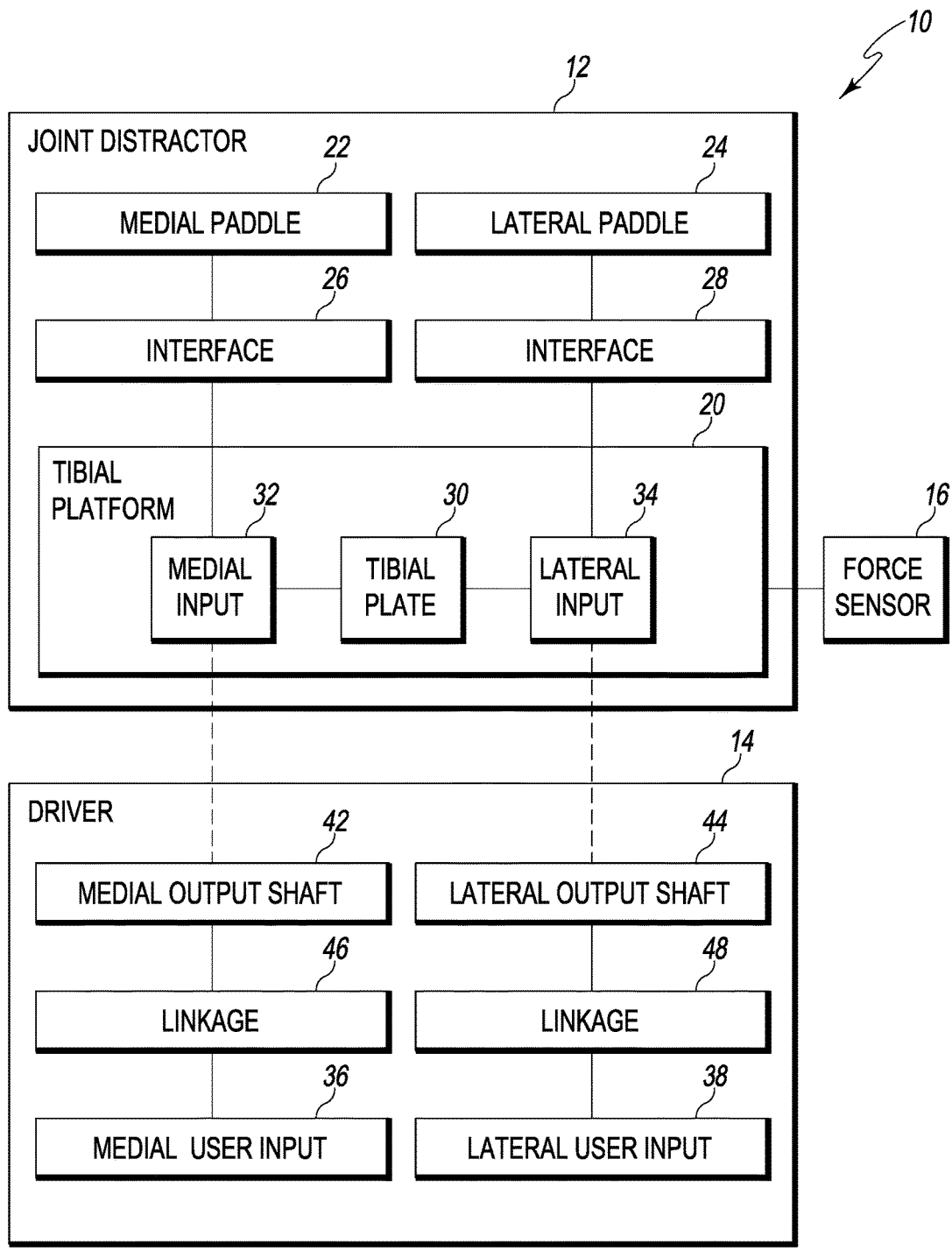
FIG. 2 is a schematic diagram of at least one embodiment of the surgical instrument of FIG. 1.

Referring now to FIG. 2, the joint distractor 12, the driver 14, and the sensor module 16 of the surgical instrumentation system 10 are shown diagrammatically. As suggested by the dashed line connection in FIG. 2, the driver 14 and the sensor module 16 are temporarily coupled or engaged with the joint distractor 12 such that the surgical instrumentation system 10 may be assembled during a surgical procedure. For example, one method of assembling the surgical instrumentation system 10 during surgery may include the steps of positioning the sensor module 16 in contact with the proximal end of a patient's tibia, positioning the joint distractor 12 on top of the sensor module 16 between a patient's femur 3 and tibia 5 to engage the proximal end of the patient's tibia and the distal end of the patient's femur, and coupling the driver 14 to the joint distractor 12.

The joint distractor 12 includes a tibial platform 20, a pair of paddles 22, 24, and a pair of interfaces 26, 28 coupled between the tibial platform 20 and the paddles 22, 24 as shown in FIG. 2. The tibial platform 20 is configured to be coupled with the driver 14 to receive user inputs during operation of the joint distractor 12 and to seat or rest on a corresponding tibial paddle of the sensor module 16 in those embodiments wherein the system 10 includes the sensor module 16. The pair of paddles 22, 24 include a medial paddle 22 and a lateral paddle 24 each configured to be placed in contact with a respective medial or lateral condyle of the patient's femur 3. The interfaces 26, 28 include a medial interface 26 and a lateral interface 28 each of which is configured to independently raise and lower a respective medial paddle 22 or lateral paddle 24 relative to the tibial platform 20 in response to a surgeon operating driver 14 as discussed in more detail below. It should be appreciated that the joint distractor 12 and driver 14 facilitate independent movement of the patient's medial and lateral femoral condyles relative to the patient's tibia.

The tibial platform 20 includes a tibial plate 30, a medial input 32, and a lateral input 34 as shown diagrammatically in FIG. 2. The tibial plate 30 is configured to be placed in contact with the proximal end of a patient's tibia and to support the medial and the lateral inputs 32, 34. The medial input 32 and the lateral input 34 are configured to be coupled to the driver 14 and to receive inputs from the driver 14 that cause respective medial and lateral paddles 22, 24 to be raised or lowered relative to the tibial plate 30.

As discussed above, the driver 14 is operabley coupleable to the distractor 12 to control operation of the distractor 12 (e.g., movement of the medial paddle 22 and lateral paddle 24). The driver 14 includes a pair of user inputs 36, 38, a pair of output shafts 42, 44, and a pair of linkages 46, 48 as shown diagrammatically in FIG. 2. The pair of user inputs 36, 38 cooperate to provide a user control 39 that includes a medial user input 36 and a lateral user input 38 each configured to independently receive a user interaction resulting in the raising or lowering of a medial or lateral condyle of a patient's femur relative to a patient's tibia. The pair of output shafts 42, 44 include a medial output shaft 42 configured to be coupled to the medial input 32 of the joint distractor 12 and a lateral output shaft 44 configured to be coupled to the lateral input 34 of the joint distractor 12. The pair of linkages 46, 48 include a medial linkage 46 and a lateral linkage 48 each of which is configured to independently drive a respective medial or lateral output shaft 42, 44 in response to a surgeon operating the medial user input 36 or the lateral user input 38 of the driver 14 such that that medial and lateral condyles of a patient's femur can be moved independently relative to the patient's tibia.

Figure 3:
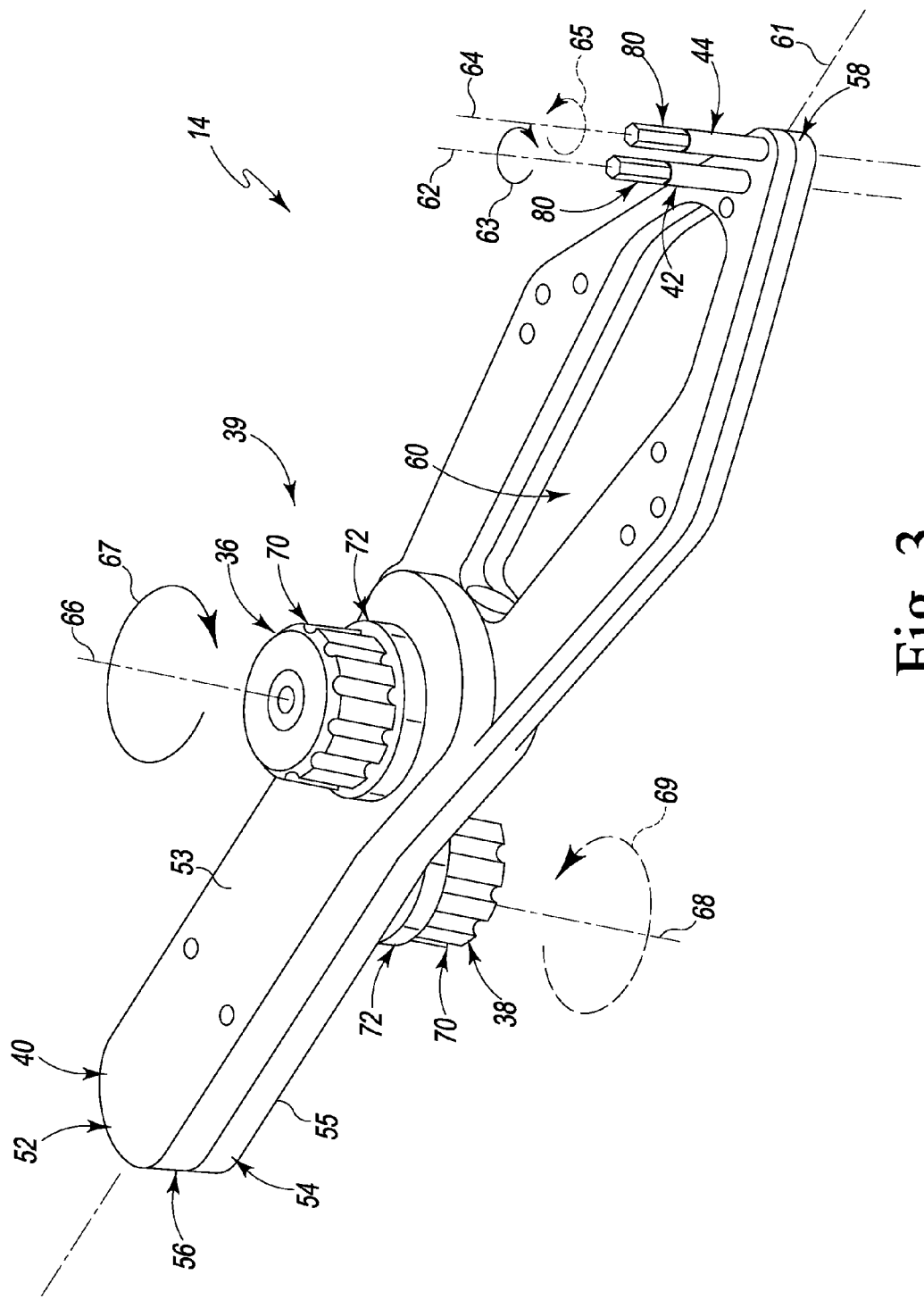
FIG. 3 is a perspective view of the driver of FIG. 1 showing that the driver includes a pair of user inputs and a pair of output shafts configured to rotate in response to a user rotating the user inputs.

In one illustrative embodiment, as shown in FIG. 3, the driver 14 includes an elongated housing 40 having a first end 56 and a second end 58 formed by an upper shell 52 and a lower shell 54. The housing 40 forms a handle 50 situated at the first end 56 of the housing 40 such that a user can hold the driver 14 while operating the joint distractor 12. The user inputs 36, 38 are coupled to the housing 40 along the handle 50 near the first end 56 of the housing 40. The output shafts 42, 44 are spaced apart from the use inputs and extend out from the housing 40 near the second end 58 of the housing 40. The housing 40 is also formed to include an access aperture 60 situated between the user inputs 36, 38 near the first end 56 of the housing 40 and the output shafts 42, 44 near the second end 58 of the housing 40. The access aperture 60 extends through the housing 40 perpendicular to a longitudinal axis 61 of the housing 40 and allows the sensor module 16 to extend through the driver 14 to be coupled to the joint distractor 12 while the joint distractor 12 is positioned between a patient's femur and tibia.

The medial user input 36 extends out from a top side 53 of the housing 40 near the first end 56 of the housing 40 as shown in FIG. 3. The lateral user input 38 extends out from a bottom side 55 of the housing 40 near the first end 56 of the housing 40. The medial output shaft 42 and the lateral output shaft 44 extend out from the top side 53 of the housing 40 near the second end 58 of the housing 40.

During operation of the driver 14, the medial output shaft 42 is rotated about an axis 62 extending along the medial output shaft 42 as suggested by solid arrow 63 in response to a user rotating the medial user input 36 about an axis 66 as suggested by solid arrow 67 shown in FIG. 3. Similarly, the lateral output shaft 44 is rotated about an axis 64 extending along the medial output shaft 44 as suggested by dashed arrow 65 in response to a user rotating the lateral user input 38 about an axis 68 as suggested by dashed arrow 69 shown in FIG. 3. Thus, a user can cause rotation of either output shaft 42, 44 independent of rotation of the other output shaft 42, 44.

Figure 4:
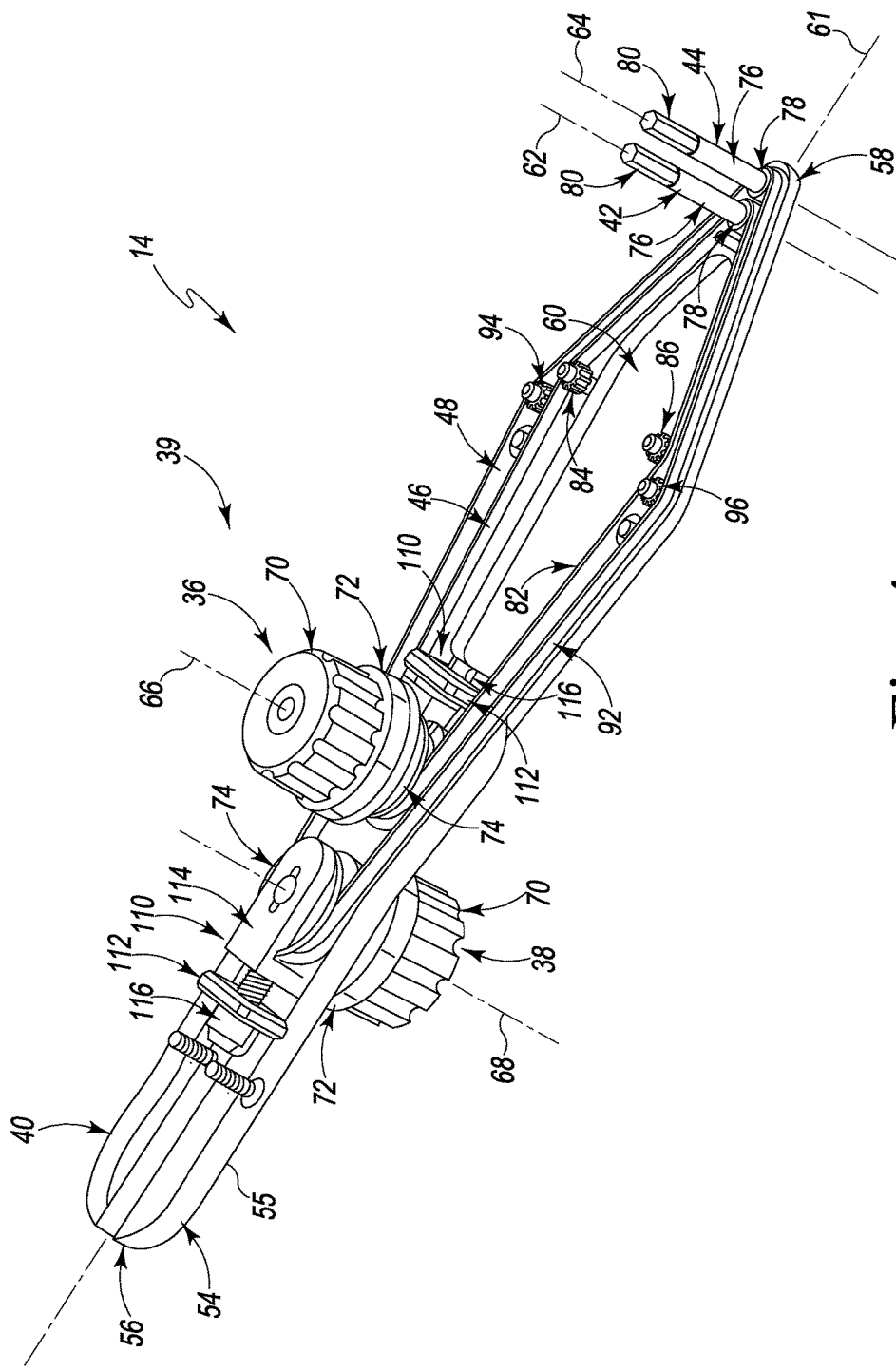
FIG. 4 is a perspective view of the driver of FIG. 3 with a top portion of a housing of the driver removed to show a pair of linkages connecting the user inputs and the output shafts.

Referring now to FIG. 4, the driver 14 is shown with the upper shell 52 of the housing 40 removed to show the internal components of the driver 14. Each of the user inputs 36, 38 are substantially similar and each includes a knob 70, an indicator ring 72, and a pulley 74 as shown in FIG. 4. The knob 70 extends outside the housing 40 of the driver 14 and is operable by a user to cause rotation of the pulley 74. The indicator ring 72 is situated outside the housing 40 and is configured to rotate in response to rotation of the knob 70 at a stepped down rate of rotation in order to indicate the amount of distraction achieved by rotation of the knob 70. The pulley 74 is situated inside of housing 40 and is coupled to a respective output shaft 42, 44 by a respective linkage 46, 48 so that the pulley 74 and its respective output shaft 42, 44 rotate at a 1 to 1 ratio.

Each of the output shafts 42, 44 are substantially similar, and each includes a shank 76 and a pulley 78 as shown in FIG. 4. The shank 76 extends out of the housing 40 of the driver 14 and is formed to include a head 80 having a hexagonal shape having six flat sides configured to be received by the medial or lateral inputs 32, 34 of the joint distractor 12. In other embodiments, the head 80 may have any shape including at least one flat side or another suitable shape that allows actuation of the medial and lateral inputs 32, 34 of the distractor 12. The pulley 78 is situated inside of housing 40 and is coupled to a respective user input 36, 38 by a respective linkage 46, 48.

The medial linkage 46 illustratively includes a belt 82 and a pair of guide rollers 84, 86 as shown in FIG. 4. The belt 82 transmits rotation from the pulley 74 of the medial user input 36 to the pulley 78 of the medial output shaft 42. The belt 82 is situated inside the housing 40 of the driver 14 and is guided by the rollers 84, 86 to extend around the access aperture 60 of the housing 40. The lateral linkage 48 illustratively includes a belt 92 and a pair of guide rollers 94, 96. The belt 92 transmits rotation from the pulley 74 of the lateral user input 38 to the pulley 78 of the lateral output shaft 44. The belt 92 is situated inside the housing 40 of the driver 14 and is guided by the rollers 94, 96 to extend around the access aperture 60 of the housing 40 and around the belt 82 of the medial linkage 46.

Figure 5:
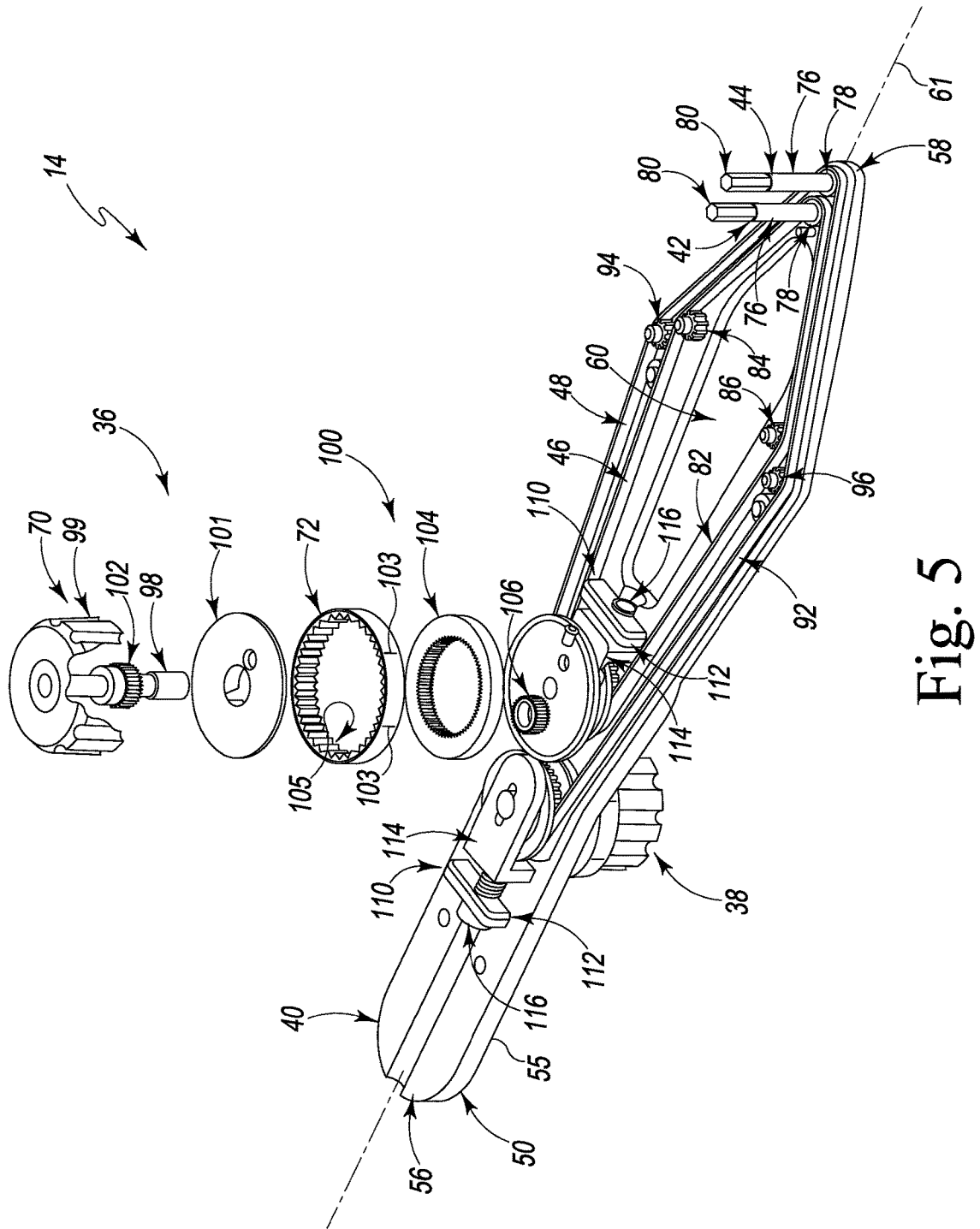
FIG. 5 is a perspective view of the driver of FIG. 4 with the user inputs disassembled showing that each user input includes a knob, an indicator ring, and a pulley.

In FIG. 5, the knob 70 and the indicator ring 72 of the medial user input 36 is disassembled from the driver 14 and the knob 70 is cut away. The knob 70 and the indicator ring 72 of the lateral use input 38 are substantially similar to the medial user input 36 and the following description is applicable to both. The knob 70 includes a shaft 98, a shell 99, and a retaining plate 101 as shown in FIG. 5. The shaft 98 is configured to couple the shell 99 to the pulley 74 so that the pulley 74 rotates with the shell 99 and to couple the shell 99 to the indicator ring 72 via a gear set 100 so that the indicator ring 72 rotates in response to rotation of the shell 99. The indicator ring 72 rotates to indicate the amount of additional (or reduced) distraction provided by the distractor 12 to the medial side of a patient's knee.

The gear set 100 is configured transmit rotation from the knob 70 to the indicator ring 72 at a reduced rate and is illustratively a planetary gear set including a central gear 102, a ring gear 104, and a planetary gear 106 as shown in FIG. 5. The central gear 102 is coupled to the shaft 98 for common rotation with the knob 70 and intermeshes with the planetary gear 106. The ring gear 104 is coupled for common rotation with the indicator ring 72 and intermeshes with the planetary gear 106. The planetary gear 106 is coupled for to a tension unit 110 supporting the pulley 74 for rotation relative thereto.

The indicator ring 72 is formed to external indicator notches 103 and internal teeth 105. The external indicator notches 103 are illustratively spaced around the indicator ring 72 to indicate about 1 mm of distraction. It should be appreciated that in other embodiments, the indicator notches 103 could be replaced with numbers, letters, or other indicators. The internal teeth 105 engage with the ring gear 104 so that the indicator ring 72 rotates with the ring gear 104. A user can "reset" or "zero" the indicator ring 72 by lifting the indicator ring 72 so that the internal teeth 105 are disengaged from the ring gear 104, setting the starting point of the indicator ring 72 by rotating the indicator ring 72 to a reset or zeroed position, and pushing the indicator ring 72 down so that the internal teeth 105 again engage the ring gear 104 and the indicator ring 72 rotates with the ring gear 104. Thus a user is able to monitor and precisely control the amount of additional (or reduced) distraction provided by the distractor 12 while operating the driver 14.

Figure 6:
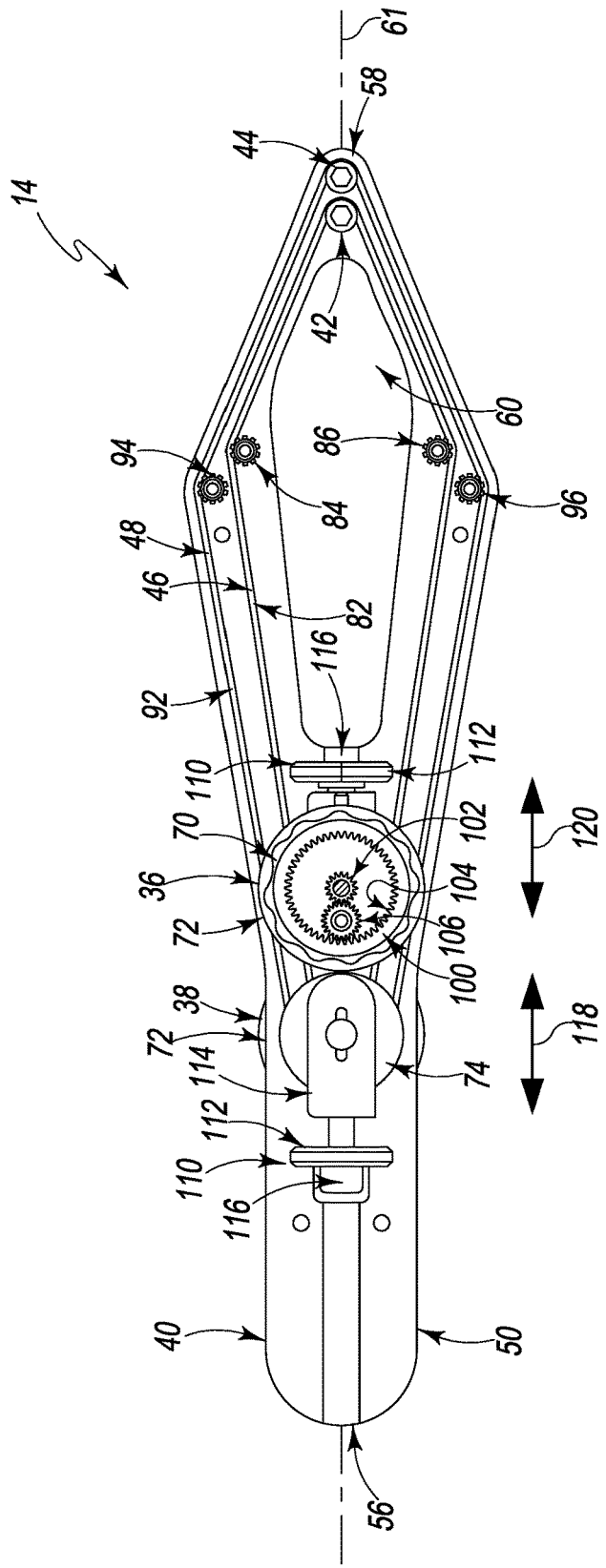
FIG. 6 is a top view of the driver of FIG. 4 with the knob cut away to show that the indicator ring is operably connected to the knob by a gear set.
Figure 7:
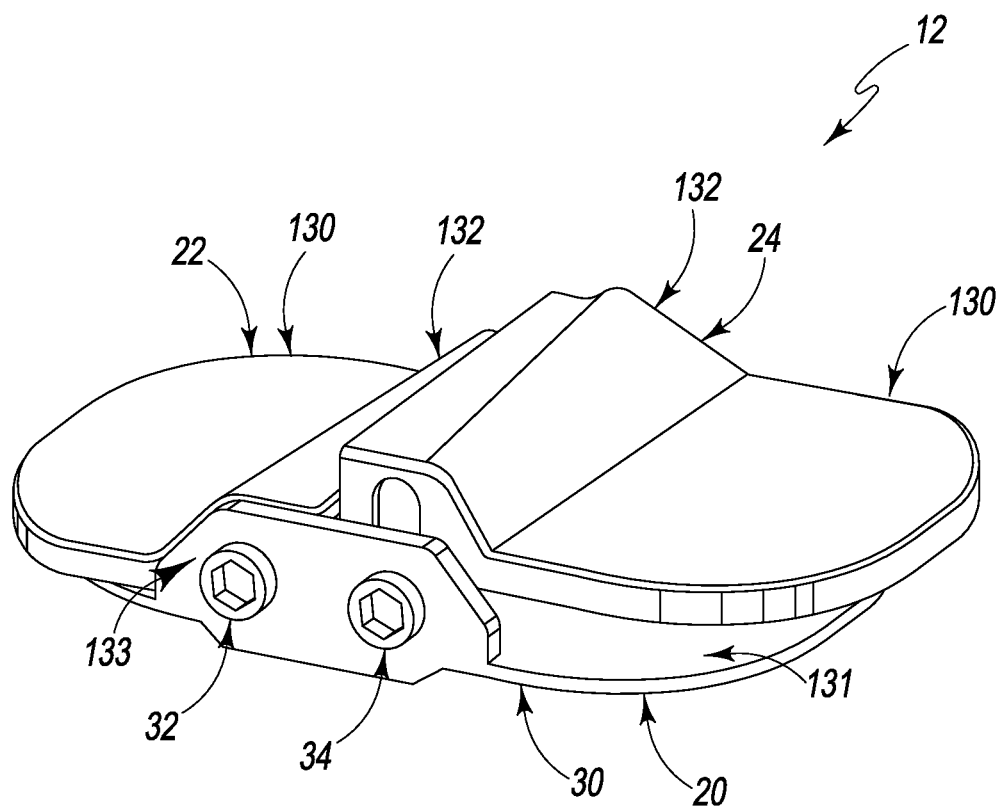
FIG. 7 is a perspective view of the joint distractor of FIG. 1 showing that the joint distractor includes a tibial platform and a pair of paddles configured to be raised and lowered relative to the tibial platform.

The knob 70 and the indicator ring 72 are cut away in FIG. 6 to show the arrangement of the gear set 100 when assembled. Illustratively, rotation of the knob 70 results in a 1 to 1 ratio of rotation passed to the pulley 74 through the shaft 98. Further, rotation of the knob 70 results in rotation of the indicator ring 72 at a ratio of less than 1 to 1 as rotation is passed through the gear set 100.

Each pulley 74 is supported by a tension unit 110 configured to allow movement of the pulleys 74 along the longitudinal axis 61 of the driver 14 to tension the belts 82, 92 as shown in FIG. 6. Each tension unit 110 includes a base plate 112, a bracket 114, and a screw 116. The base plates 112 are coupled to the housing 40 of the driver 14 along the longitudinal axis 61 of the driver 14. The brackets 114 support the pulleys 74 and are moved along the longitudinal axis 61 of the driver 14 as suggested by arrows 118, 120 in response to rotation of the screws 116. The screws 116 extend through the base plates 112 and threadably engage the brackets 114 so that the brackets 114 are moved in response to rotation of the screws 116.

Turning now to FIGS. 7-10, the joint distractor 12 of the illustrative embodiment is shown in detail. The joint distractor 12 is configured to space the medial and lateral condyles of a patient's femur from the patient's tibia at desired distances to orient the knee joint. The medial paddle 22 and the lateral paddle 24 of the joint distractor 12 are movable independently relative to the to the tibial platform 20 to allow a user to position the medial and lateral condyles of a patient's femur at different distances from the proximal end of a patient's tibia as suggested in FIG. 7 thereby orienting the knee joint to obtain a desirable mechanical and anatomic axis of the knee joint.

Figure 8:
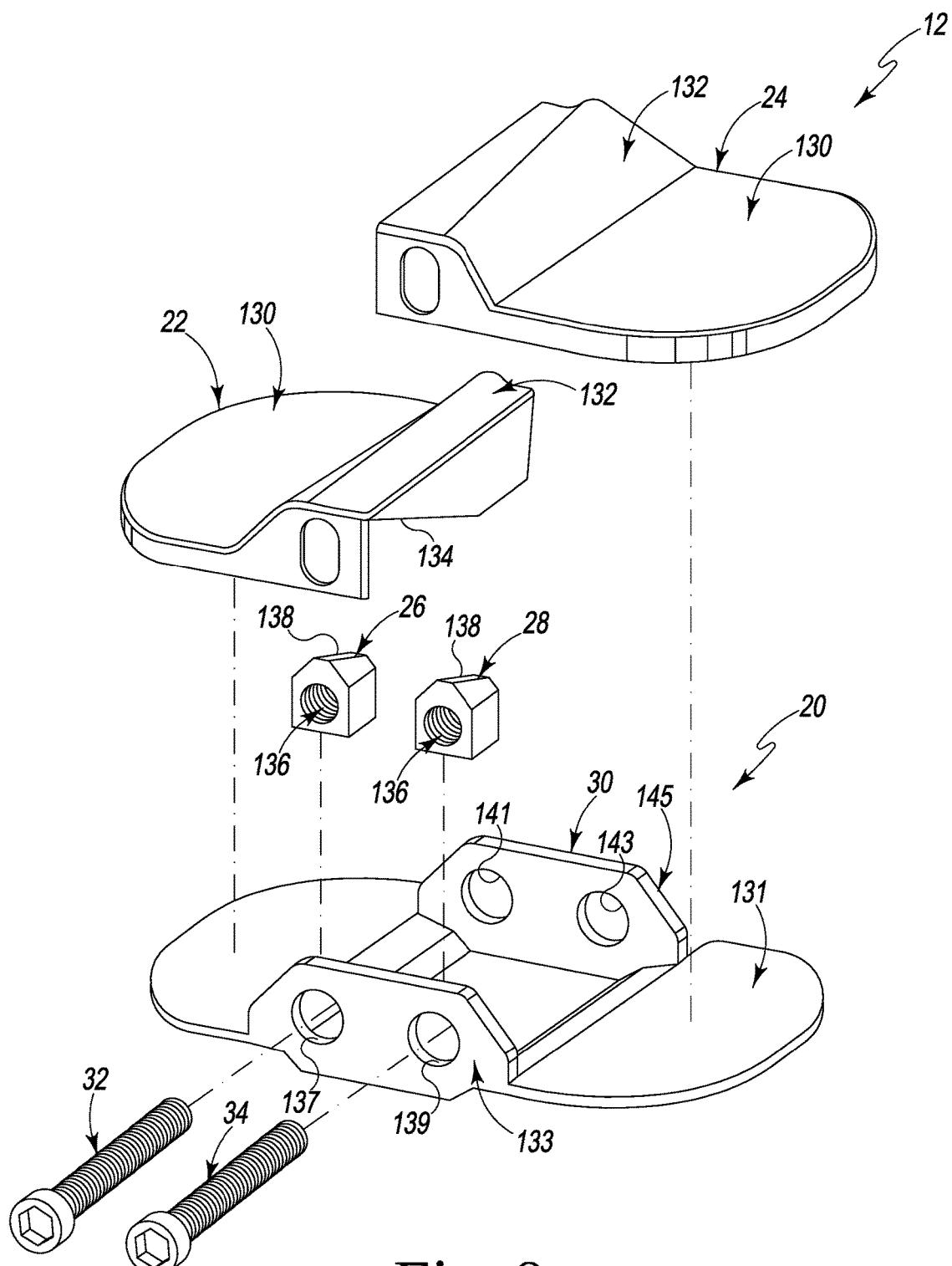
FIG. 8 is an exploded view of the joint distractor of FIG. 7.

The tibial platform 20 of the joint distractor 12 includes a tibial plate 30, a medial input 32, and a lateral input 34 as shown in FIG. 8. In some embodiments, the tibial plate 30 may be formed to include a cavity 122 (see FIGS. 9 and 10) along the underside of the tibial plate 30 sized to receive the sensor module 16. In the illustrative embodiment, the medial input 32 is embodied as a medial input screw 32 and the lateral input 34 is embodied as a lateral input screw 34. Each illustrative input screw 32, 34 is configured to mate with the heads 80 of the output shafts 42, 44 of the driver 14 and are coupled to the tibial plate 30 to rotate relative to the tibial plate 30.

The tibial plate 30 includes a bottom panel 131, a front panel 133, and a back panel 145 as shown in FIG. 8. The bottom panel 131 is configured to engage a patient's proximal tibia during surgery. The front panel 133 extends up from the bottom panel 131 along an anterior side of the bottom panel 131 and includes holes 137, 139 configured to support input screws 32, 34. The back panel 145 extends up from the bottom panel 131 along a posterior side of the bottom panel 133 and includes holes 141, 143 configured to support input screws 32, 34.

The medial paddle 22 and the lateral paddle 24 of the joint distractor 12 are each formed to include an outer surface 130 and a central surface 132 as shown in FIG. 8. The outer surfaces 130 of the paddles 22, 24 are configured to contact the medial and lateral condyles of a patient's femur during surgery. The central surfaces 132 of the paddles 22, 24 extend up from the outer portions 130 and are configured to be situated between the medial and lateral condyles of a patient's femur during surgery. The central surfaces 132 of the paddles 22, 24 also form a downwardly-facing ramp surface 134 configured to interact with the medial and lateral inputs 32, 34 to raise and lower the paddles 22, 24 independently.

In the illustrative embodiment, the medial interface 26 and the lateral interface 28 are embodied as interface blocks 26, 28 as shown in FIG. 8. Each interface block 26, 28 is formed to include a threaded hole 136 and an upwardly-facing ramp surface 138. The threaded holes 136 of the medial and lateral interface blocks 26, 28 are configured to mate with the threads of the medial and lateral input screws 32, 34. The upwardly-facing ramp surfaces 138 of the medial and lateral interfaces 26, 28 are configured to mate with, or otherwise contact, the downwardly-facing ramp surfaces 134 of the medial and lateral paddles 22, 24.

Figure 9:
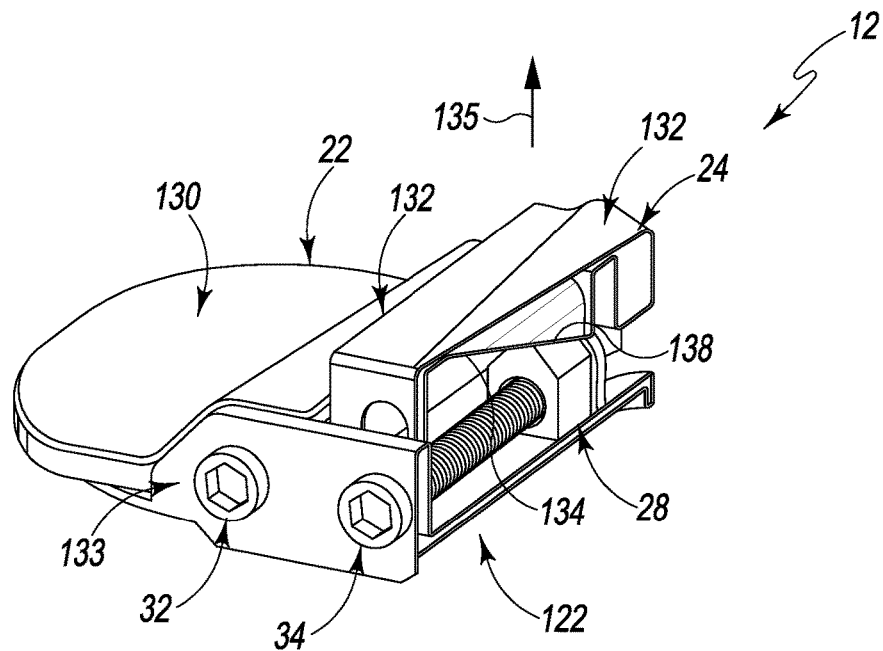
FIG. 9 is a perspective view of the joint distractor of FIG. 7 showing the internal components of the joint distractor when a lateral paddle moved to a raised position relative to the tibial platform.

In operation, each of the paddles 22, 24 are configured to move between a raised position and a lowered position as illustrated by the lateral paddle 24 in FIGS. 8 and 9. For brevity, only operation of the lateral components 24, 28, 34 of the joint distractor 12 are further discussed, however the following description is equally applicable to the lateral components 22, 26, 32 of the joint distractor 12.

When the lateral paddle 24 is in the raised position, the lateral input screw 34 has been rotated in a first direction in order to move the lateral interface block 28 along the lateral input screw 34 to a posterior position as shown in FIG. 9. With the lateral interface block 28 in the posterior position, the upwardly-facing ramp surface 138 of the lateral interface block 28 pushes the downwardly-facing ramp surface 134 of the lateral paddle 24 up thereby lifting the lateral paddle 24 vertically up from the tibial plate 30 as suggested by arrow 135 in FIG. 9.

Figure 10:
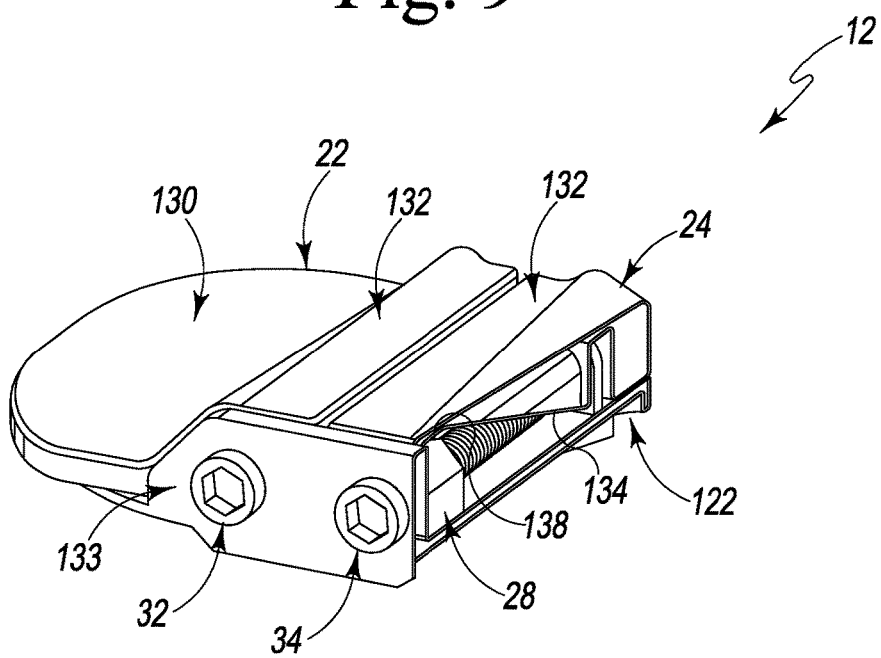
FIG. 10 is a perspective view of the joint distractor of FIG. 8 when the lateral paddle is moved to a lowered position relative to the tibial platform.

When the lateral paddle 24 is in the lowered position, the lateral input screw 34 has been rotated in a second direction in order to move the lateral interface block 28 along the lateral input screw 34 to an anterior position as shown in FIG. 10. With the lateral interface block 28 in the anterior position, the upwardly-facing ramp surface 138 of the lateral interface block 28 slides along the downwardly-facing ramp surface 134 of the lateral paddle 24 thereby allowing the lateral paddle 24 to move vertically down toward the tibial plate 30 as suggested in FIG. 10.

Figure 11:
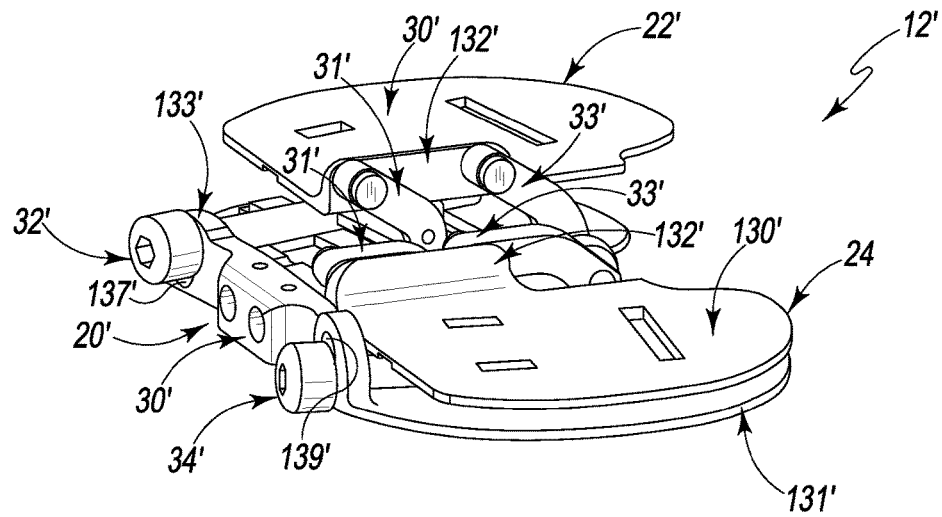
FIG. 11 is a perspective view of another joint distractor for use with the driver of FIGS. 3-6, the joint distractor including a tibial platform and a pair of paddles configured to be raised and lowered relative to the tibial platform.
Figure 12:
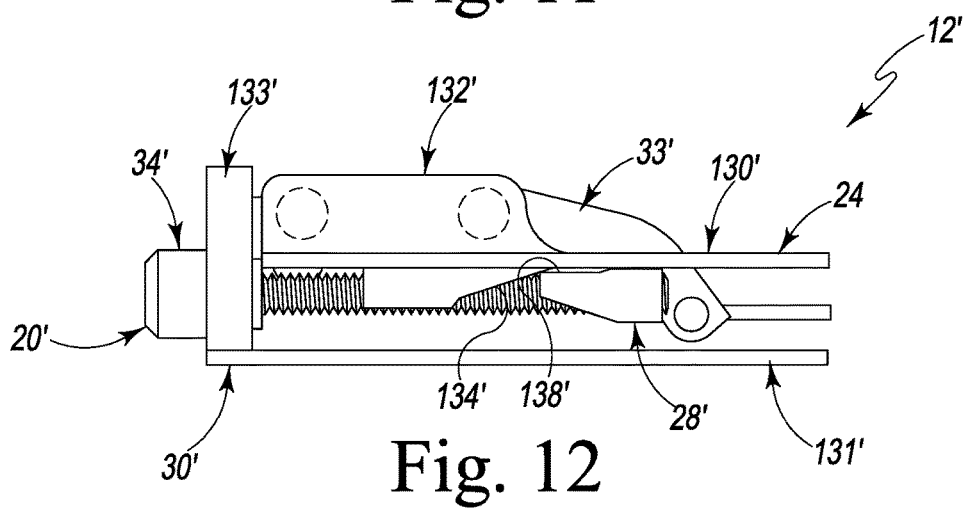
FIG. 12 is a side elevation view of the joint distractor of FIG. 11 showing the components of the joint distractor when a lateral paddle moved to a lowered and anterior position relative to the tibial platform.
Figure 13:
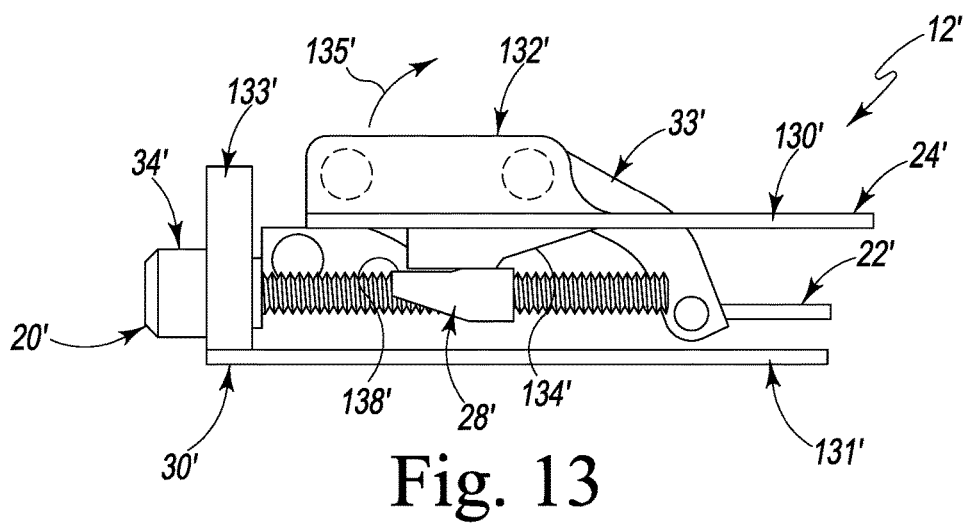
FIG. 13 is a perspective view of the joint distractor of FIG. 12 when the lateral paddle is moved to a raised and posterior position relative to the tibial platform.

Another illustrative joint distractor 12', which is configured to be used with the driver 14, is shown in FIGS. 11-13. The joint distractor 12' includes a tibial platform 20', a pair of paddles 22', 24', and a pair of interfaces 26', 28' coupled between the tibial platform 20' and the paddles 22', 24' as shown in FIG. 11. The tibial platform 20' is configured to be coupled with the driver 14 to receive user inputs during operation of the joint distractor 12' and to the sensor module 16 to support the sensor module 16 during surgery. The paddles 22', 24' are illustratively embodied as a medial paddle 22' and a lateral paddle 24', each of which is configured to be placed in contact with a respective medial or lateral condyle of the patient's femur. The interfaces 26', 28' include a medial interface 26' and a lateral interface 28', each of which is configured to independently raise and lower a respective medial or lateral paddle 22', 24' relative to the tibial platform 20' in response to a surgeon operating driver 14 so that medial and lateral condyles of a patient's femur can be moved independently relative to the patient's tibia to orient a patient's knee joint.

The tibial platform 20' includes a tibial plate 30', a medial input 32', and a lateral input 34' as shown in FIG. 11. The tibial plate 30' is configured to be placed in contact with the proximal end of a patient's tibia or sensor module 16. The medial input 32' and the lateral input 34' are configured to be coupled to the driver 14 and to receive interaction (e.g., the turning of the inputs 32', 34') from the driver 14 that cause respective medial and lateral paddles 22', 24' to be raised or lowered relative to the tibial plate 30'.

The tibial plate 30' includes a bottom panel 131' and a front panel 133' as shown in FIG. 11. The bottom panel 131' is configured to engage a patient's proximal tibia during surgery. The front panel 133' extends up from the bottom panel 131' along an anterior side of the bottom panel 131' and includes holes 137', 139' configured to support input screws 32', 34'.

In the illustrative embodiment, the medial input 32' is embodied as a medial input screw 32', and the lateral input 34' is embodied as a lateral input screw 34'. Each illustrative input screw 32', 34' is configured to mate with the heads 80 of the output shafts 42, 44 and are coupled to the tibial plate 30' to rotate relative to the tibial plate 30'.

The medial paddle 22' and the lateral paddle 24' of the joint distractor 12 are each formed to include an outer surface 130' and a central surface 132' as shown in FIG. 8. The outer surfaces 130' of the paddles 22', 24' are configured to contact the medial and lateral condyles of a patient's femur during surgery. The central surfaces 132' of the paddles 22', 24' extend up from the outer portions 130' and are configured to be situated between the medial and lateral condyles of a patient's femur during surgery. The central surfaces 132' of the medial paddle 22' and the lateral paddle 24' of the joint distractor 12' are coupled to tibial plate 30' by a pair of swing arms 31', 33'. The swing arms 31', 33' guide movement of the paddles 22', 24' so that the paddles 22', 24' move along an arcuate path when raised and lowered relative to the tibial plate 30'. The central portions 132' of the paddles 22', 24' also form a downwardly-facing ramp surface 134' configured to interact with the medial and lateral inputs 32', 34' to raise and lower the paddles 22', 24' independently.

In the illustrative embodiment, the medial interface 26' and the lateral interface 28' are interface blocks 26', 28' as shown in FIG. 11. Each interface block 26', 28' is formed to include a threaded hole 136' and an upwardly-facing ramp surface 138'. The threaded holes 136' of the medial and lateral interface blocks 26', 28' are configured to mate with the threads of the medial and lateral input screws 32', 34'. The upwardly-facing ramp surfaces 138' of the medial and lateral interfaces 26', 28' are configured to mate with the downwardly-facing ramp surfaces 134' of the medial and lateral paddles 22', 24'.

In operation, each of the paddles 22', 24' is configured to move between a raised position and a lowered position as illustrated by the lateral paddle 24' in FIGS. 12-13. For brevity, only operation of the lateral components 24', 28', 34' of the joint distractor 12' are further discussed, however the following description is equally applicable to the lateral components 22', 26', 32' of the joint distractor 12'.

When the lateral paddle 24' is in the lowered position, the lateral input screw 34' is rotated in a first direction in order to move the lateral interface block 28' along the lateral input screw 34' to a posterior position as shown in FIG. 12. With the lateral interface block 28' in the posterior position, the upwardly-facing ramp surface 138' of the lateral interface block 28' slides along the downwardly-facing ramp surface 134' of the lateral paddle 24' thereby allowing the lateral paddle 24' to move down and forward along an arcuate path toward the tibial plate 30' to an anterior and lowered position as shown in FIG. 12.

When the lateral paddle 24' is in the raised position, the lateral input screw 34' is rotated in a second direction in order to move the lateral interface block 28' along the lateral input screw 34' to an anterior position as shown in FIG. 13. With the lateral interface block 28' in the anterior position, the upwardly-facing ramp surface 138' of the lateral interface block 28' engages the downwardly-facing ramp surface 134' of the lateral paddle 24' thereby lifting the lateral paddle 24' up and back along an arcuate path from the tibial plate 30' to a raised and posterior position as suggested by arrow 135' in FIG. 13.

Figure 14:
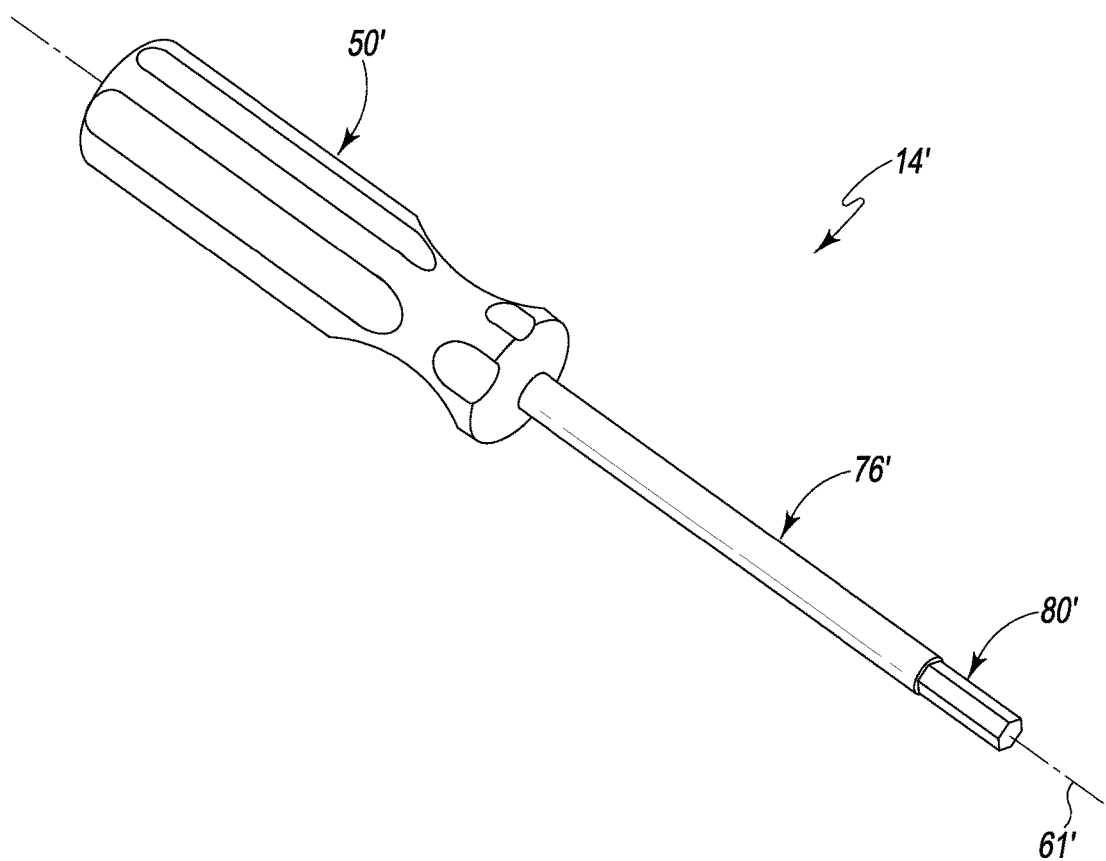
FIG. 14 is a perspective view of an alternative driver for use with the joint distractors of FIGS. 7-12.

Turning now to FIG. 14, another driver 14' configured for use with the joint distractors 12, 12' is shown. The driver 14' includes a handle 50' and a shank 76' defining a longitudinal axis 61' of the driver 14'. The handle 50' is coupled to the shank 76' and provides a structure that a healthcare provider may grasp during operation. The shank 76' is formed to include a head 80' spaced apart from the handle 50'. The head 80' illustratively has a hexagonal shape with six flat sides configured to be received by the medial or lateral inputs 32, 34 of the joint distractor 12 or the other medial or lateral inputs 32', 34' of the other joint distractor 12'. In other embodiments, the head 80' may have any other shape having at least one flat side or another suitable shape.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

The invention claimed is:

1. An orthopedic surgical instrument system comprising:
    an elongated body having a first end and a second end, the elongated body defining a longitudinal axis and having a handle at the first end;
    a first output shaft extending out from a first side of the elongated body along a first output axis substantially perpendicular to the longitudinal axis of the elongated body;
    a second output shaft extending out from the first side of the elongated body along a second output axis substantially perpendicular to the longitudinal axis of the elongated body;
    a user control coupled to the elongated body near the first end of the elongated body, and
    a joint distractor having a tibial platform, a first paddle and a second paddle,
    wherein the first output shaft and the second output shaft are situated near the second end of the elongated body, and the first output shaft and the second output shaft are configured to turn independent of one another in response to operation of the user control, and
    wherein the first output shaft is configured to move the first paddle relative to the tibial platform and the second output shaft is configured to move the second paddle relative to the tibial platform.

2. The orthopedic surgical instrument system of claim 1, wherein the user control comprises a first input and a second input.

3. The orthopedic surgical instrument system of claim 2, wherein the first output shaft is configured to turn in response to a user operating the first input and the second output shaft is configured to turn in response to a user operating the second input.

4. The orthopedic surgical instrument system of claim 3, wherein the first input includes a first pulley housed inside the elongated body and rotatable about a first input axis that extends perpendicular to the longitudinal axis of the elongated body.

5. The orthopedic surgical instrument system of claim 4, wherein the second input includes a second pulley housed inside the elongated body and rotatable about a second input axis spaced apart from the first input axis that extends perpendicular to the longitudinal axis of the elongated body.

6. The orthopedic surgical instrument system of claim 5, further comprising a first belt linkage connecting the first pulley to the first output shaft and a second belt linkage connecting the second pulley to the second output shaft.

7. The orthopedic surgical instrument system of claim 6, wherein the first pulley is movable along the longitudinal axis of the elongated body to tension the first belt linkage and the second pulley is movable along the longitudinal axis of the elongated body to tension the second belt linkage.

8. The orthopedic surgical instrument system of claim 6, wherein the first input comprises a knob coupled to the first pulley and rotatable about the first input axis.

9. The orthopedic surgical instrument system of claim 1, wherein the first output axis and the second output axis are coplanar.

10. The orthopedic surgical instrument system of claim 1, wherein the first output shaft includes a proximal end coupled to the elongated body and a distal end having a driver head with at least one planar surface extending along the first output axis, and the second output shaft includes a proximal end coupled to the elongated body and a distal end having a driver head with at least one planar surface extending along the first output axis.

11. The orthopedic surgical instrument system of claim 1, wherein the elongated body is formed to include an access aperture extending through the elongated body substantially perpendicular to the longitudinal axis of the elongated body, the access aperture situated between the user control and the second end of the elongated body.

12. An orthopedic surgical instrument comprising:
    an elongated body having a first end and a second end, the elongated body defining a longitudinal axis and having a handle at the first end;

a first output shaft extending out from a first side of the elongated body along a first output axis substantially perpendicular to the longitudinal axis of the elongated body;

a second output shaft extending out from the first side of the elongated body along a second output axis substantially perpendicular to the longitudinal axis of the elongated body; and a user control coupled to the elongated body near the first end of the elongated body, the user control including a first input and a second input, wherein the first output shaft and the second output shaft are situated near the second end of the elongated body, and the first output shaft and the second output shaft are configured to turn independent of one another in response to operation of the user control, and wherein the first input includes a knob, an indicator ring, and a gear set coupled between the knob and the indicator ring so that the indicator ring turns less than one revolution in response to the knob being turned one revolution.

13. The orthopedic surgical instrument of claim 12, wherein the first output shaft is configured to turn in response to a user operating the first input and the second output shaft is configured to turn in response to a user operating the second input.

14. The orthopedic surgical instrument of claim 13, wherein the first input includes a first pulley housed inside the elongated body and rotatable about a first input axis that extends perpendicular to the longitudinal axis of the elongated body.

15. The orthopedic surgical instrument of claim 14, wherein the second input includes a second pulley housed inside the elongated body and rotatable about a second input axis spaced apart from the first input axis that extends perpendicular to the longitudinal axis of the elongated body.

16. The orthopedic surgical instrument of claim 15, further comprising a first belt linkage connecting the first pulley to the first output shaft and a second belt linkage connecting the second pulley to the second output shaft.

17. The orthopedic surgical instrument of claim 16, wherein the first pulley is movable along the longitudinal axis of the elongated body to tension the first belt linkage and the second pulley is movable along the longitudinal axis of the elongated body to tension the second belt linkage.

18. The orthopedic surgical instrument of claim 16, wherein the first input comprises a knob coupled to the pulley and rotatable about the first input axis.

19. The orthopedic surgical instrument of claim 12, wherein the first output shaft includes a proximal end coupled to the elongated body and a distal end having a driver head with at least one planar surface extending along the first output axis, and the second output shaft includes a proximal end coupled to the elongated body and a distal end having a driver head with at least one planar surface extending along the first output axis.

20. The orthopedic surgical instrument of claim 12, wherein the elongated body is formed to include an access aperture extending through the elongated body substantially perpendicular to the longitudinal axis of the elongated body, the access aperture situated between the user control and the second end of the elongated body.

* * * * *